United States Patent
Boukhny

(10) Patent No.: US 7,572,242 B2
(45) Date of Patent: Aug. 11, 2009

(54) METHOD OF OPERATING AN ULTRASOUND HANDPIECE

(75) Inventor: Mikhail Boukhny, Laguna Niguel, CA (US)

(73) Assignee: Alcon, Inc., Hunenberg (CH)

( * ) Notice: Subject to any disclaimer, the term of this patent is extended or adjusted under 35 U.S.C. 154(b) by 194 days.

(21) Appl. No.: 11/207,642

(22) Filed: Aug. 19, 2005

(65) Prior Publication Data

US 2005/0277869 A1    Dec. 15, 2005

Related U.S. Application Data

(63) Continuation-in-part of application No. 11/183,591, filed on Jul. 18, 2005, which is a continuation-in-part of application No. 10/916,675, filed on Aug. 12, 2004, application No. 11/207,642, which is a continuation-in-part of application No. 10/818,314, filed on Apr. 5, 2004, now Pat. No. 7,297,137.

(60) Provisional application No. 60/555,240, filed on Mar. 22, 2004.

(51) Int. Cl.
*A61B 17/20* (2006.01)

(52) U.S. Cl. .......................... 604/22; 606/169

(58) Field of Classification Search .......... 604/22, 604/544; 606/169, 166, 170, 171, 27, 129
See application file for complete search history.

(56) References Cited

U.S. PATENT DOCUMENTS

| 3,526,219 A | 9/1970 | Balamuth |
| 3,589,363 A | 6/1971 | Banko |
| 3,601,126 A | 8/1971 | Estes et al. |
| 3,693,613 A | 9/1972 | Kelman |
| 3,812,855 A | 5/1974 | Banko |
| 3,812,858 A | 5/1974 | Oringer |
| 3,857,387 A | 12/1974 | Shock |
| 3,902,495 A | 9/1975 | Weiss et al. |
| 3,930,505 A | 1/1976 | Wallach |
| 3,942,519 A | 3/1976 | Shock |
| 3,952,732 A | 4/1976 | Shock |
| 3,956,826 A | 5/1976 | Perdreaux, Jr. |
| 3,964,487 A | 6/1976 | Judson |
| 3,990,452 A | 11/1976 | Murry et al. |
| 4,024,467 A | 5/1977 | Andrews et al. |

(Continued)

FOREIGN PATENT DOCUMENTS

EP    359217    3/1990

(Continued)

OTHER PUBLICATIONS

Shuyu, Lin. "Sandwiched Piezoelectric Ultrasonic Transducers of Longitudinal-Torsional Compound Vibrational Modes." *IEEE Transactions of Ultrasonics, Ferroelectrics and Frequency Control*, Nov. 1997, pp. 1189-1197.

(Continued)

*Primary Examiner*—Nicholas D Lucchesi
*Assistant Examiner*—Laura A Bouchelle
(74) *Attorney, Agent, or Firm*—Kenneth D. Bassinger

(57) ABSTRACT

A method of operating an ultrasonic handpiece by pulsing the power supplied to the handpiece and varying the amplitude of the power during the power pulse.

13 Claims, 4 Drawing Sheets

U.S. PATENT DOCUMENTS

| | | | |
|---|---|---|---|
| 4,024,866 A | 5/1977 | Wallach |
| 4,114,623 A | 9/1978 | Meinke et al. |
| 4,126,137 A | 11/1978 | Archibald |
| 4,156,187 A | 5/1979 | Murry et al. |
| 4,168,707 A | 9/1979 | Douvas et al. |
| 4,184,510 A | 1/1980 | Murry et al. |
| 4,223,676 A | 9/1980 | Wuchinich |
| 4,246,902 A | 1/1981 | Martinez |
| 4,248,232 A | 2/1981 | Engelbrecht et al. |
| 4,406,284 A | 9/1983 | Banko |
| 4,417,578 A | 11/1983 | Banko |
| 4,493,694 A | 1/1985 | Wuchinich |
| 4,496,342 A | 1/1985 | Banko |
| 4,504,264 A | 3/1985 | Kelman |
| 4,508,532 A | 4/1985 | Drews et al. |
| 4,515,583 A | 5/1985 | Sorich |
| 4,589,415 A | 5/1986 | Haaga |
| 4,590,935 A | 5/1986 | Ranalli |
| 4,609,368 A | 9/1986 | Dotson, Jr. |
| 4,651,280 A | 3/1987 | Chang et al. |
| 4,658,819 A | 4/1987 | Harris et al. |
| 4,705,500 A | 11/1987 | Reimels et al. |
| 4,712,544 A | 12/1987 | Ensslin |
| 4,739,759 A | 4/1988 | Rexroth et al. |
| 4,750,488 A | 6/1988 | Wuchinich et al. |
| 4,770,654 A | 9/1988 | Rogers et al. |
| 4,793,346 A | 12/1988 | Mindich |
| 4,827,911 A | 5/1989 | Broadwin et al. |
| 4,869,715 A | 9/1989 | Sherburne |
| 4,922,902 A | 5/1990 | Wuchinich et al. |
| 4,961,424 A | 10/1990 | Kubota et al. |
| 4,969,885 A | 11/1990 | Farin |
| 4,989,583 A | 2/1991 | Hood |
| 4,989,588 A | 2/1991 | Kubota et al. |
| 5,026,387 A | 6/1991 | Thomas |
| 5,116,343 A | 5/1992 | Ams et al. |
| 5,139,509 A | 8/1992 | Fischer et al. |
| 5,151,085 A | 9/1992 | Sakurai et al. |
| 5,154,694 A | 10/1992 | Kelman |
| 5,154,696 A | 10/1992 | Shearing |
| 5,160,317 A | 11/1992 | Costin |
| 5,180,363 A | 1/1993 | Idemoto et al. |
| 5,188,102 A | 2/1993 | Idemoto et al. |
| 5,205,817 A | 4/1993 | Idemoto et al. |
| 5,222,959 A | 6/1993 | Anis |
| 5,242,385 A | 9/1993 | Strukel |
| 5,279,547 A | 1/1994 | Costin |
| 5,304,115 A | 4/1994 | Pflueger et al. |
| 5,342,293 A | 8/1994 | Zanger |
| 5,359,996 A | 11/1994 | Hood |
| 5,431,664 A | 7/1995 | Ureche et al. |
| 5,520,633 A | 5/1996 | Costin |
| 5,569,188 A | 10/1996 | Mackool |
| 5,591,127 A | 1/1997 | Barwick, Jr. et al. |
| 5,676,649 A | 10/1997 | Boukhny et al. |
| 5,700,240 A | 12/1997 | Barwick, Jr. et al. |
| 5,722,945 A | 3/1998 | Anis et al. |
| 5,733,256 A | 3/1998 | Costin |
| 5,766,146 A | 6/1998 | Barwick, Jr. |
| 5,808,396 A | 9/1998 | Boukhny |
| 5,865,790 A | 2/1999 | Bair |
| 6,027,515 A | 2/2000 | Cimino |
| 6,028,387 A | 2/2000 | Boukhny |
| 6,077,285 A | 6/2000 | Boukhny |
| 6,083,193 A | 7/2000 | Kadziauskas et al. |
| 6,175,180 B1 | 1/2001 | Angelini et al. |
| 6,179,808 B1 | 1/2001 | Boukhny et al. |
| 6,193,683 B1 | 2/2001 | Ludin et al. |
| 6,261,283 B1 | 7/2001 | Morgan et al. |
| 6,261,297 B1 | 7/2001 | Kadziauskas et al. |
| 6,283,974 B1 | 9/2001 | Alexander |
| 6,315,755 B1 | 11/2001 | Sussman |
| 6,402,769 B1 * | 6/2002 | Boukhny .................... 606/169 |
| 6,629,948 B2 | 10/2003 | Rockley |
| 6,699,212 B1 | 3/2004 | Kadziauskas |
| 6,780,165 B2 | 8/2004 | Kadziauskas et al. |
| 7,374,552 B2 | 5/2008 | Wuchinich |
| 2001/0001123 A1 | 5/2001 | Madan et al. |
| 2001/0011176 A1 | 8/2001 | Boukhny |
| 2003/0045887 A1 | 3/2003 | Sakurai et al. |
| 2004/0092800 A1 | 5/2004 | MacKool |
| 2004/0092922 A1 * | 5/2004 | Kadziauskas et al. ......... 606/27 |
| 2006/0041200 A1 | 2/2006 | Dotter et al. |

FOREIGN PATENT DOCUMENTS

| | | |
|---|---|---|
| WO | 8705793 | 10/1987 |
| WO | WO 92/07622 | 5/1992 |
| WO | WO 99/45868 | 9/1999 |
| WO | WO 01/41672 | 6/2001 |
| WO | WO 2004/080505 | 9/2004 |

OTHER PUBLICATIONS

Jiromaru Tsujino, "Ultrasonic Motor Using A One-Dimensional Longitudinal-Torsional Vibration Converter With Diagonal Slits", Smart Mater. Struct. 7 (1998) 345-351.

* cited by examiner

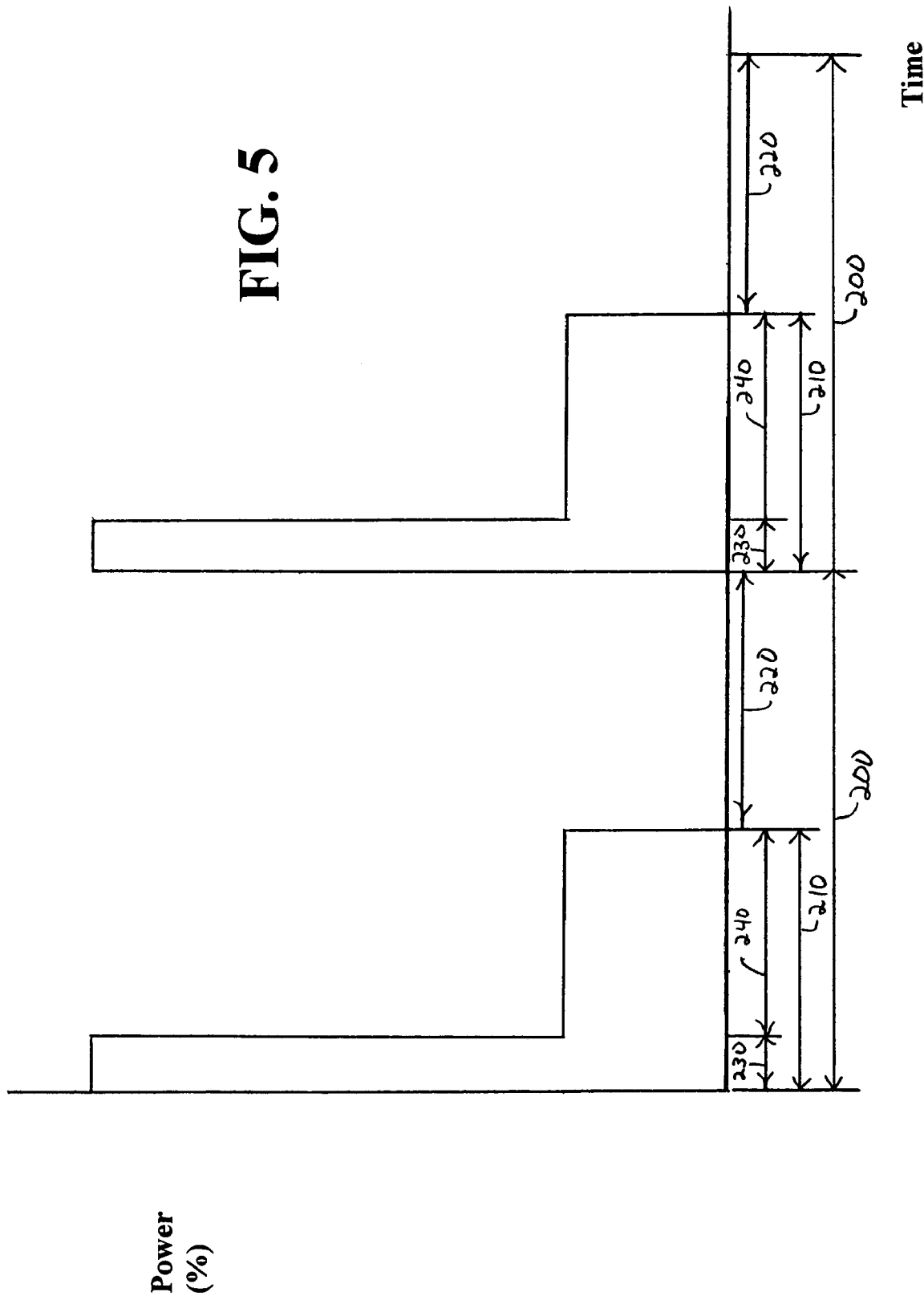

METHOD OF OPERATING AN ULTRASOUND HANDPIECE

This application is a continuation-in-part of U.S. patent application Ser. No. 11/183,591, filed Jul. 18, 2005, currently co-pending, which is a continuation-in-part application of U.S. patent application Ser. No. 10/916,675, filed Aug. 12, 2004, currently co-pending. This application is also is a continuation-in-part of co-pending U.S. patent application Ser. No. 10/818,314, filed Apr. 5, 2004, now U.S. Pat. No. 7,297, 137, priority to which is claimed under 35 U.S.C. §120, which claims priority to U.S. Provisional Application Ser. No. 60/555,240, filed Mar. 22, 2004, under 35 U.S.C. §119. This application also claims priority under 35 U.S.C. §119 to U.S. Provisional Application Ser. No. 60/587,693, filed Jul. 14, 2004.

BACKGROUND OF THE INVENTION

This invention relates to ultrasonic devices and more particularly to devices for tuning and controlling an ophthalmic phacoemulsification handpiece.

A typical ultrasonic surgical device suitable for ophthalmic procedures consists of an ultrasonically driven handpiece, an attached hollow cutting tip, an irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece at its nodal points by relatively inflexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246, 902; 4,493,694; 4,515,583; 4,589,415; 4,609,368; 4,869,715; and 4,922,902, the entire contents of which are incorporated herein by reference.

When used to perform phacoemulsification, the ends of the cutting tip and irrigating sleeve are inserted into a small incision of predetermined width in the cornea, sclera, or other location in the eye tissue in order to gain access to the anterior chamber of the eye. The cutting tip is ultrasonically vibrated along its longitudinal axis within the irrigating sleeve by the crystal-driven ultrasonic horn, thereby emulsifying upon contact the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the bore of the cutting tip, the horn bore, and the aspiration line and into a collection device. The aspiration of emulsified tissue is aided by a saline flushing solution or irrigant that is injected into the surgical site through the small annular gap between the inside surface of the irrigating sleeve and the outside surface of the cutting tip.

There have been prior attempts to combine ultrasonic longitudinal motion of the cutting tip with rotational motion of the tip, see U.S. Pat. No. 5,222,959 (Anis), U.S. Pat. No. 5,722,945 (Anis, et al.) and U.S. Pat. No. 4,504,264 (Kelman), the entire contents of which are incorporated herein by reference. These prior attempts have used electric motors to provide the rotation of the tip which require O-ring or other seals that can fail in addition to the added complexity and possible failure of the motors.

There have also been prior attempts to generate both longitudinal and torsional motion without the use of electric motors. For example, in U.S. Pat. Nos. 6,028,387, 6,077,285 and 6,402,769 (Boukhny), one of the inventors of the current invention, describes a handpiece having two pairs of piezoelectric crystals are used. One pair is polarized to product longitudinal motion. The other pair is polarized to produce torsional motion. Two separate drive signals are used to drive the two pairs of crystals. In actual practice, making a handpiece using two pairs of crystals resonate in both longitudinal and torsional directions is difficult to achieve. One possible solution, also described by one of the current inventors, is described in U.S. Patent Publication No. US 2001/0011176 A1 (Boukhny). This reference discloses a handpiece have a single set of piezoelectric crystals that produces longitudinal motion, and a series of diagonal slits on the handpiece horn or tip that produce torsional motion when the horn or tip is driven at the resonate frequency of the piezoelectric crystals. Again, in practice, the resonate frequency of the piezoelectric crystals and the tip or horn did not coincide, so simultaneous longitudinal and torsional motion was difficult to achieve.

When the tip becomes occluded or clogged with emulsified tissue, the aspiration flow can be reduced or eliminated, allowing the tip to heat up, thereby reducing cooling and resulting in temperature increase, which may burn the tissue at the incision. In addition, during occlusion, a larger vacuum can build up in the aspiration tubing so that when the occlusion eventually breaks, a larger amount of fluid can be quickly suctioned from the eye, possibly resulting in the globe collapsing or other damage to the eye.

Known devices have used sensors that detect large rises in aspiration vacuum, and detect occlusions based a particular pre-determined vacuum level. Based on this sensed occlusion, power to the handpiece may be reduced and/or irrigation and aspiration flows can be increased. See U.S. Pat. Nos. 5,591,127, 5,700,240 and 5,766,146 (Barwick, Jr., et al.), the entire contents of which are incorporated herein by reference. These devices, however, use a fixed aspiration vacuum level to trigger a response from the system. This fixed level is a threshold value based upon a fixed percentage of the selected upper vacuum limit. The use and effectiveness of such systems, however, are limited since they do not respond until that preset vacuum level is reached. In addition, some surgical techniques require the plugging or occlusion of the tip, and the occurrence of an occlusion does not necessarily indicate that the tip and/or wound is getting heated sufficiently to create a concern or a thermal injury or burn at the wound site.

U.S. Pat. No. 4,827,911 (Broadwin, et al.) and U.S. Pat. No. 6,780,165 B2 (Kadziauskas, et al.) suggests that the risk of a thermal injury can be reduced by delivering the ultrasound energy in pulses of very short duration follow by a period wherein no energy is delivered to the tip. Such short pulses can help reduce the amount of energy entering the eye, but as the pulses get shorter, there is less time for the feedback loop to establish the optimum frequency. Current ultrasound handpiece tuning systems use a feedback loop to monitor the operation of the handpiece and continually tune the handpiece to ensure that the stock of the tip remains constant under all loading conditions. See U.S. Pat. No. 5,431,664 (Ureche, et al.). Such feedback loops typically take on the order of 3-5 milliseconds to cycle and automatically adjust the operating parameters of the handpiece. As a result, with current systems, ultrasonic power pulses of less than 5 milliseconds have limited ability to establish the optimum frequency, but in general, improvements to the tuning algorithm can be achieved for pulse durations of less than 20 milliseconds.

Accordingly, a need continues to exist for a reliable ultrasonic handpiece that is capable of delivering ultrasound pulses of less than 5 milliseconds while remaining in tune.

BRIEF SUMMARY OF THE INVENTION

The present invention improves upon prior art methods of operating an ultrasonic handpiece by pulsing the power supplied to the handpiece and varying the amplitude of the power during the power pulse.

It is accordingly an object of the present invention to provide a method for operating a pulsed ultrasound handpiece.

It is a further object of the present invention to provide a method of operating an ultrasound handpiece that delivers ultrasound pulses of less than 5 milliseconds while remaining in tune.

Other objects, features and advantages of the present invention will become apparent with reference to the drawings, and the following description of the drawings and claims.

BRIEF DESCRIPTION OF THE DRAWINGS

FIGS. 4 and 5 are graphs illustrating ultrasound power versus time.

DETAILED DESCRIPTION OF THE INVENTION

Figure 1:
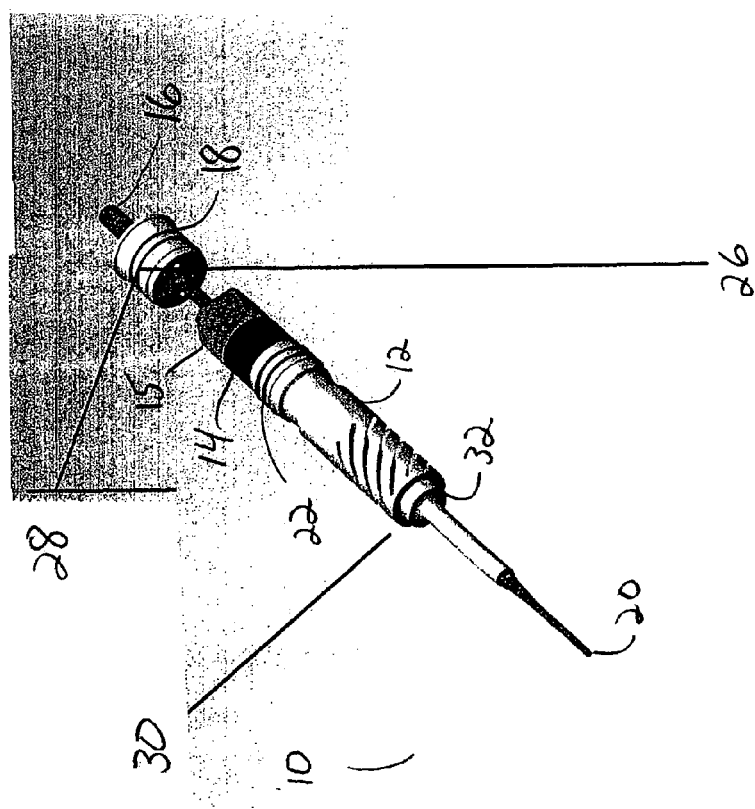
FIG. 1 is a perspective view of the handpiece of the present invention with the outer case removed.

As best seen in FIG. 1 handpiece 10 that may be used with the method of the present invention generally comprises ultrasonic horn 12, typically made from a titanium alloy. Horn 12 has a plurality of helical slits, which will be discussed below. A plurality (typically 1 or 2 pairs) of ring-shaped piezoelectric elements 14 are held by compression nut 15 against horn 12. Aspiration shaft 16 extends down the length of handpiece 10 through horn 12, piezoelectric elements 14, nut 15 and through plug 18 at the distal end of handpiece 10. Aspiration tube 16 allows material to be aspirated through hollow tip 20, which is attached to horn 12, and through and out handpiece 10. Plug 18 seals outer shell 11 of handpiece 10 fluid tight, allowing handpiece 10 to be autoclaved without adversely affecting piezoelectric elements 14. Addition grooves 22 for sealing O-ring gaskets (not shown) are provided on horn 12.

Figure 2:
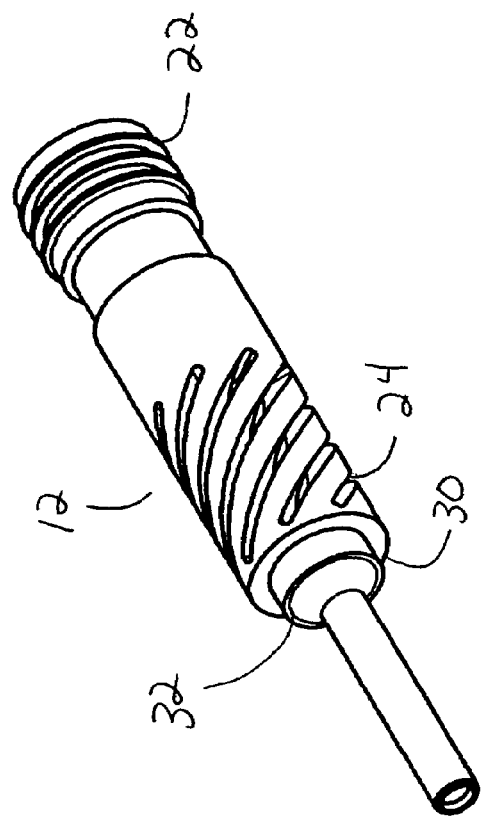
FIG. 2 is a perspective view of the ultrasonic horn that may be used with the handpiece of the present invention.

As best seen in FIG. 2, horn 12 contains a plurality of spiral slits 24. Preferably, the width of slits 24 is between 2% and 65% of the outside diameter of horn 12. This, of course, will affect how many slits 24 can be made on horn 12 (e.g., if slits 24 are 65% of the diameter of horn 12, then only one slit 24 may be cut into horn 12). The width of slits 24 selected will depend upon the desired amount of torsional movement. The depth of slits 24 in horn 12 preferably is between 4% and 45% of the outside diameter of horn 12. Slits 24 may have a flat or square cut bottom, but preferably have a rounded or radiused bottom, which are easier to manufacture. The length of slits 24 preferably is between 8% and 75% of the length of the larger diameter of horn 12. The pitch of slits 24 preferably is between 125% and 500% of the larger diameter of horn 12. By way of example, the inventors have found that one suitable configuration of slits 24 on horn 12 with an outside diameter of 0.475 inches is a total of eight slits 24, having a width of 0.04 inches, a depth of 0.140 (with a full radius bottom), a length of 0.7 inches and a pitch of 1.35 inches gives suitable torsional movement of horn 12 without compromising the longitudinal movement of horn 12.

As best seen in FIG. 1, the location of longitudinal and torsional nodal points (the points with zero velocity of the respective mode) is important for proper functioning of handpiece 10. The torsional node 26 preferably is located at the proximal longitudinal node 28, so that the torsional node 26 and the longitudinal node 28 are coincident, e.g., both of which are located on plug 18. Handpiece 10 also contains a distal longitudinal node 30 located at reduced diameter portion 32 of horn 12.

Figure 3:
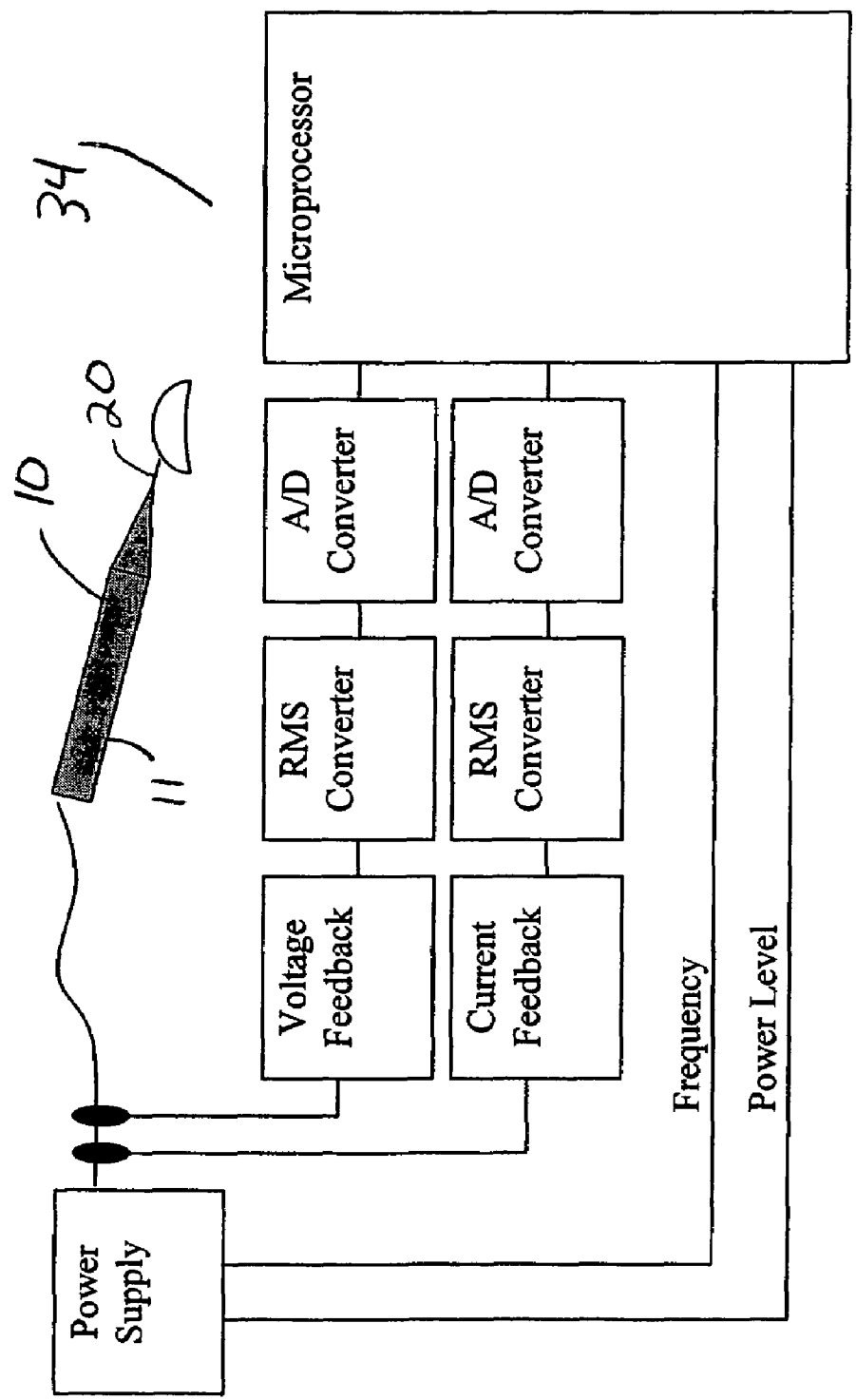
FIG. 3 a block diagram of a driving circuit that may be used with the present invention.

As best seen in FIG. 3, drive circuit 34 that may be used with handpiece 10 of the present invention preferably is similar to that described in U.S. Pat. No. 5,431,664, the entire contents of which being incorporated herein by reference, in that drive circuit 34 provides a drive signal to handpiece 10 and tracks the admittance of handpiece 10 and controls the frequency of handpiece 10 to maintain a constant admittance. However, drive circuit 34 monitors both the torsional mode and the longitudinal mode and controls these modes in handpiece 10 using two different drive frequencies. Preferably, the torsional drive signal is approximately 32 kHz and the longitudinal drive signal is 44 kHz, but these frequencies will change depending upon the piezoelectric elements 14 used and the size and shape of horn 12 and slits 24. Although both the longitudinal or the torsional drive signal may be supplied in a continuous manner, preferably the longitudinal drive signal and the torsion drive signal are alternated, so that the drive signal is provided in a desired pulse at one frequency and then switched to the other frequency for a similar pulse, with no overlap between the two frequencies, but no gap or pause in the drive signal. Alternative, the drive signal can be operated in a similar manner as described, but short pauses or gaps in the drive signal can be introduced. In addition, the amplitude of the drive signal can be modulated and set independently for each frequency.

The pause or gap between drive signals can serve various purposes. One purpose is to allow for the ultrasound movement of piezoelectric elements 14 and horn 12 to attenuate or stop so that lens fragments can once again be suctioned to tip 20 and an occlusion reestablished, thereby increasing the holding force on the lens fragment. Reestablishing the occlusion will increase cutting efficiency of the following pulse of ultrasound, whether longitudinal or torsional. Another purpose of the pause or gap between drive signals is to allow for the ultrasound movement of piezoelectric elements 14 and horn 12 to attenuate or stop prior to the other (either longitudinal. or torsional) mode being excited. Such attenuation between drive signals will reduce amount of potential non-linear interactions in the system which can generate undesirable heat and lead to premature degradation of piezoelectric elements 14 or mechanical failure of the entire assembly.

Alternatively, there can be a slight overlap in the longitudinal and torsional drive signals. The overlap may provide relatively short time intervals when the added action of both torsional and longitudinal displacements results in especially fast rate of lens emulsification, and yet the overlap is short enough to prevent piezoelectric elements 14 from premature degradation or failure of the entire mechanical assembly as a result of excessive stress.

Yet another alternative if to have both longitudinal and torsional drive signals overlap completely thus resulting in applying high stress levels to the lens material when the two signals overlap, and yet leaving a pause in between for the occlusion to reestablish itself and allow for vacuum to build-up, thus improving efficiency of the following pulse application.

Still another alternative is to apply a continuous longitudinal signal with a pulsed torsional signal, or vice versa, a continuous torsional signal with a pulsed longitudinal signal. Continuous application of torsional ultrasound does not cause repulsion because tip 20 movement is oriented perpendicular to the direction of the engagement of tip 20 with the lens, and the pulsed applications of longitudinal ultrasound are short enough to prevent overheating or mechanical damage to piezoelectric elements 14.

Finally, as discussed above, both the longitudinal and torsional drive signals can be applied continuously and simultaneously, with the amplitudes of the both signals being selected such that overheating and excessive mechanical stress on the system is reduced. If such a drive scheme is to be used, two sets of piezoelectric elements 14 are preferred with the torsional signal being applied to one set, while longitudinal signal applied to the other set.

Figure 4:
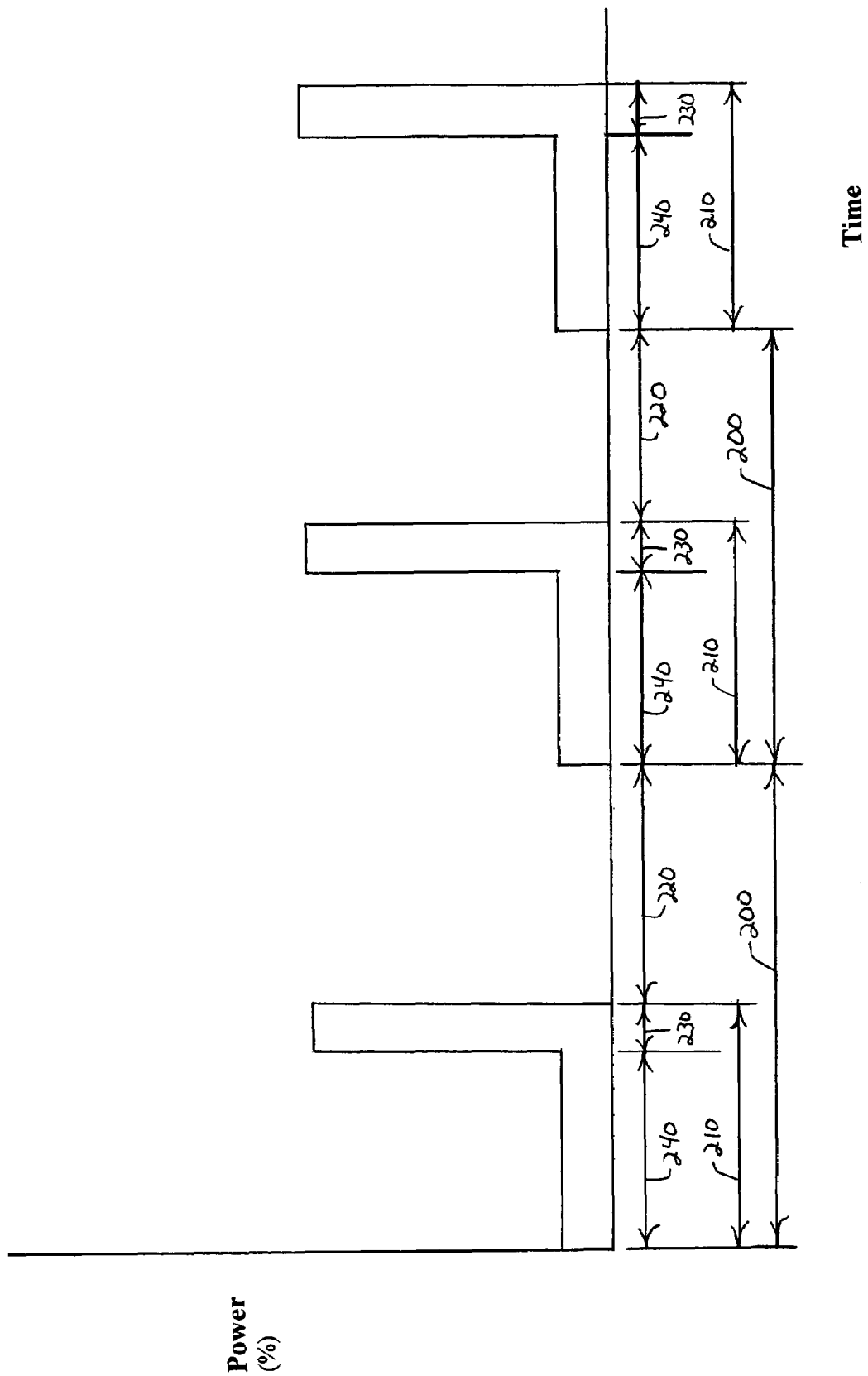

As best seen in FIGS. 4 and 5, typical duty cycle 200 includes power on portion 210 and power off portion 220. By way of example, FIG. 4 illustrates a 50% duty cycle 200, meaning that on portion 210 equals off portion 220. The inventor has discovered that the power level (which may be measured as a percent of the maximum possible stroke or rotation of the tip, or as a percentage of the maximum amplitude of the power signal delivered to piezoelectric elements 14), within on portion 210 may be further divided into high power portion 230 and low power portion 240. By way of example, high power portion 230 may be at a 60% power level and low power portion 240 may be at a 10% power level. Such a division of on portion 210 allows high power portion 230 to be of extremely short duration, for example, between 1 millisecond and 5 milliseconds, and preferably less than 5 milliseconds, while the overall duration of on portion 210 may remain relatively long, for example, 20 milliseconds or greater. Maintaining a relatively long on portion 210 allows the feedback loop contained within drive circuit 34 sufficient time to cycle and automatically adjust the operating parameters of handpiece 10. Further, because low power portion 240 encompasses a significant percentage of on power portion 210, on the order of 75% to 95%, maintaining a relatively long on power portion 210 does not significantly increase the heat generated by tip 20. As a result, ultrasonic power pulses of less than 5 milliseconds are possible while maintaining the optimum frequency for handpiece 10 while at the same time, the potential for thermal injury to the eye is reduced.

One skilled in the art will recognize that both high power portion 230 and low power portion 240 may be include longitudinal or torsional vibration of tip 20 in any combination desired. In addition, while FIGS. 4 and 5 demonstrate on power portion 210 as having one high power portion 230 and one low power portion 240, on power portion 210 may be further sub-divided into multiple high power portions 230 and/or multiple low power portions 240, serially, alternately or randomly.

While certain embodiments of the present invention have been described above, these descriptions are given for purposes of illustration and explanation. Variations, changes, modifications and departures from the systems and methods disclosed above may be adopted without departure from the scope or spirit of the present invention.

I claim:

1. A method of operating an ultrasound handpiece, comprising the steps of:
   a) providing an ultrasound handpiece;
   b) providing an ultrasound drive circuit capable of producing an ultrasound drive signal;
   c) delivering the ultrasound drive signal to the ultrasound handpiece in a series of pulses so as to produce periodic ultrasound vibrations in the ultrasound handpiece, each period of ultrasound vibrations in the ultrasound handpiece being followed by a period of no ultrasound vibrations in the ultrasound handpiece; and
   d) varying the power level of the ultrasound vibrations in the ultrasound handpiece during the periodic ultrasound vibrations in the ultrasound handpiece wherein varying the power level of the ultrasound vibrations in the ultrasound handpiece comprises dividing the periodic ultrasound vibrations in the handpiece into at least a first, low power torsional pulse period to avoid repulsion of lens material, followed by a second, high power longitudinal pulse period.

2. The method of claim 1 wherein the period of ultrasound vibrations in the ultrasound handpiece is at least 20 milliseconds.

3. The method of claim 1 wherein the high power period is less than 5 milliseconds.

4. The method of claim 1 wherein the period of ultrasound vibrations in the ultrasound handpiece is of variable duration.

5. The method of claim 1 wherein the period of no ultrasound vibrations in the ultrasound handpiece is of variable duration.

6. A method of operating an ultrasound handpiece, comprising the steps of:
   a) providing an ultrasound handpiece;
   b) providing an ultrasound drive circuit capable of producing an ultrasound drive signal;
   c) delivering the ultrasound drive signal to the ultrasound handpiece in a series of pulses so as to produce periodic ultrasound vibrations in the ultrasound handpiece; and
   d) varying the power level of the ultrasound vibrations in the ultrasound handpiece during the periodic ultrasound vibrations in the ultrasound handpiece wherein varying the power level of the ultrasound vibrations in the ultrasound handpiece comprises dividing the periodic ultrasound vibrations in the handpiece into at least a first, low power torsional pulse period to avoid repulsion of lens material, followed by a second, high power longitudinal pulse period.

7. The method of claim 6 wherein the period of ultrasound vibrations in the ultrasound handpiece is at least 20 milliseconds.

8. The method of claim 6 wherein the high power period is less than 5 milliseconds.

9. The method of claim 6 wherein the period of ultrasound vibrations in the ultrasound handpiece is of variable duration.

10. A method of operating an ultrasound hand piece, the method comprising:
   providing an ultrasound hand piece;
   providing a drive circuit capable of producing an ultrasound drive signal;
   delivering the ultrasound drive signal in a series of pulses so as to produce periodic ultrasound vibrations in the ultrasound hand piece;
   varying the power level of the ultrasound vibrations in the ultrasound hand piece during the periodic ultrasound vibrations in the ultrasound hand piece by dividing the periodic ultrasound vibrations in the hand piece into at least a first, low power torsional pulse period followed by a second, high power longitudinal pulse period; and
   avoiding repulsion of lens material at a tip of the ultrasound hand piece by providing an ultrasound drive signal that results in torsional movement of the tip.

11. The method of claim 10 wherein the period of ultrasound vibrations in the ultrasound hand piece is at least 20 milliseconds.

12. The method of claim 10 wherein the high power period is less than 5 milliseconds.

13. The method of claim 10 wherein the period of ultrasound vibrations in the ultrasound hand piece is of variable duration.

* * * * *